US010139991B2

(12) United States Patent
Chander et al.

(10) Patent No.: US 10,139,991 B2
(45) Date of Patent: Nov. 27, 2018

(54) LIGHTWEIGHT VIRTUAL ENVIRONMENT

(71) Applicant: FUJITSU LIMITED, Kawasaki-shi, Kanagawa (JP)

(72) Inventors: Ajay Chander, San Francisco, CA (US); Sanam Mirzazad Barijough, Mountain View, CA (US)

(73) Assignee: FUJITSU LIMITED, Kawasaki (JP)

( * ) Notice: Subject to any disclaimer, the term of this patent is extended or adjusted under 35 U.S.C. 154(b) by 203 days.

(21) Appl. No.: 15/088,072

(22) Filed: Mar. 31, 2016

(65) Prior Publication Data
US 2017/0285887 A1    Oct. 5, 2017

(51) Int. Cl.
G06F 3/0482 (2013.01)
G06F 3/0481 (2013.01)
G06Q 10/10 (2012.01)
G16H 50/30 (2018.01)
G06F 19/00 (2018.01)

(52) U.S. Cl.
CPC ........ G06F 3/0482 (2013.01); G06F 3/04817 (2013.01); G06F 19/00 (2013.01); G06Q 10/10 (2013.01); G16H 50/30 (2018.01)

(58) Field of Classification Search
CPC ........................... G06F 3/04817; G06F 3/0482
See application file for complete search history.

(56) References Cited

U.S. PATENT DOCUMENTS

| | | |
|---|---|---|
| 5,554,033 A | 9/1996 | Bizzi et al. |
| 6,425,764 B1 | 7/2002 | Lamson |
| 7,873,485 B2 | 1/2011 | Castelli et al. |
| 2003/0101075 A1* | 5/2003 | Ban .................. G06Q 10/10 705/2 |
| 2010/0075807 A1* | 3/2010 | Hwang ............ G06F 19/3481 482/8 |
| 2016/0054876 A1 | 2/2016 | Robison |

OTHER PUBLICATIONS

European Search Report for corresponding application No. 16204935.7, dated May 29, 2017.

(Continued)

Primary Examiner — Jeffrey A Gaffin
Assistant Examiner — Ayesha Huertas Torres
(74) Attorney, Agent, or Firm — Maschoff Brennan

(57) ABSTRACT

A method includes receiving input data pertaining to a user. Based on the input data, the method includes rendering a graphical user interface (GUI) that includes an initial icon arrangement (arrangement) presentable in a virtual environment. The initial icon arrangement includes a set of icons representative of portions of an overall time period represented by the initial icon arrangement. The method includes determining whether a portion of the input data is representable in the initial icon arrangement. If so, the method includes quantifying the second portion of the input data with a target and a timeframe, associating the target and the timeframe with the second portion of the input data, modifying icons in the arrangement that correspond to the timeframe to represent the target, rendering the modified icons as an opportunity layer on the arrangement, and displaying the arrangement with the opportunity layer in the virtual environment.

20 Claims, 11 Drawing Sheets

(56) References Cited

OTHER PUBLICATIONS

Bailey, J.O., Bailenson, J.N., Flora, J., Armel, K.C., Voelker, D., & Reeves, B. (2015). "The Impact of Vivid Messages on Reducing Energy Consumption Related to Hot Water Use", SAGE Publications, vol. 47(5), doi: 10.1177/0013916514551604. Apr. 20, 2015, pp. 570-592.

Rosenberg RS, Baughman SL, Bailenson JN (2013), "Virtual Superheroes: Using Superpowers in Virtual Reality to Encourage Prosocial Behavior". PLoS One 8(1): e55003. doi:10.1371/journal.pone.0055003, Jan. 30, 2013.

Anuj K. Shah et al. (2012), "Some Consequences of Having Too Little. Science", American Association for the Advancement of Science, print ISSN 0036-8075; online ISSN 1095-9203, doi: 10.1126/science.1222426.

\* cited by examiner

LIGHTWEIGHT VIRTUAL ENVIRONMENT

FIELD

The embodiments discussed herein are related to lightweight virtual environment.

BACKGROUND

Multiple sensors may be implemented to measure data related to behaviors of users. However, measurement and presentation of data related to behavior of the user does not necessarily result in improved behavior outcomes. Indeed, awareness of data does not necessarily result in changes in behavior of the user.

Virtual environments (VE) may be developed to create a connection between a user and a virtual entity. The connection between the user and the virtual entity may enable the virtual entity to influence a behavior of the user through interaction in the VE. However, VEs are expensive and complex. For instance, VEs may include visual, olfactory, voice, and graphical environments. Moreover, the VEs may be customized to a particular user, which may reduce an ability of other users to interact with the VE.

The subject matter claimed herein is not limited to embodiments that solve any disadvantages or that operate only in environments such as those described above. Rather, this background is only provided to illustrate one example technology area where some embodiments described herein may be practiced.

SUMMARY

According to an aspect of an embodiment, a method may include receiving, at a virtual environment (VE) device, input data pertaining to a user. The input data may include user contributed data input to a user input device and machine contributed data measured at one or more sensors. Based on a first portion of the input data, the method may include rendering by the VE device, a graphical user interface (GUI) that includes an initial icon arrangement presentable in a virtual environment. The initial icon arrangement may include a set of icons that are each representative of a particular portion of an overall time period represented by the initial icon arrangement. The method may include determining, by the VE device, whether a second portion of the input data is representable in the initial icon arrangement. In response to the second portion of input data being representable, the method may include: quantifying the second portion of the input data with a target and a timeframe, associating the target with the second portion of the input data, associating the timeframe with the second portion of the input data, modifying one or more icons of the set of icons in the initial icon arrangement that correspond to the timeframe to represent the target, rendering the modified icons as an opportunity layer on the initial icon arrangement, and displaying, on a display device, the initial icon arrangement with the opportunity layer in the virtual environment.

The object and advantages of the embodiments will be realized and achieved at least by the elements, features, and combinations particularly pointed out in the claims.

It is to be understood that both the foregoing general description and the following detailed description are exemplary and explanatory and are not restrictive of the invention, as claimed.

BRIEF DESCRIPTION OF THE DRAWINGS

Example embodiments will be described and explained with additional specificity and detail through the use of the accompanying drawings in which.

DESCRIPTION OF EMBODIMENTS

Sensors may be implemented to measure data related to behaviors of users. However, measurement and presentation of data related to behavior of the user does not necessarily result in improved behavior outcomes. Indeed, awareness of data does not necessarily result in changes in behavior of the user. Accordingly, some embodiments described in this disclosure are configured to present data related to behaviors of the users in a way that primes scarcity to the user. Scarcity may be a motivating factor that may improve the behavior outcomes of the user. These and other embodiments may include a lightweight graphical user interface (GUI) that presents and displays data that pertains to the user. The GUI may be generated based on user contributed data and machine contributed data. The GUI may be updated through dynamic re-rendering based on updated data that are subsequently measured.

This and other embodiments are described herein with reference to the appended drawings. In the appended drawings, items similarly numbered have similar structures unless discussed otherwise.

Figure 1:
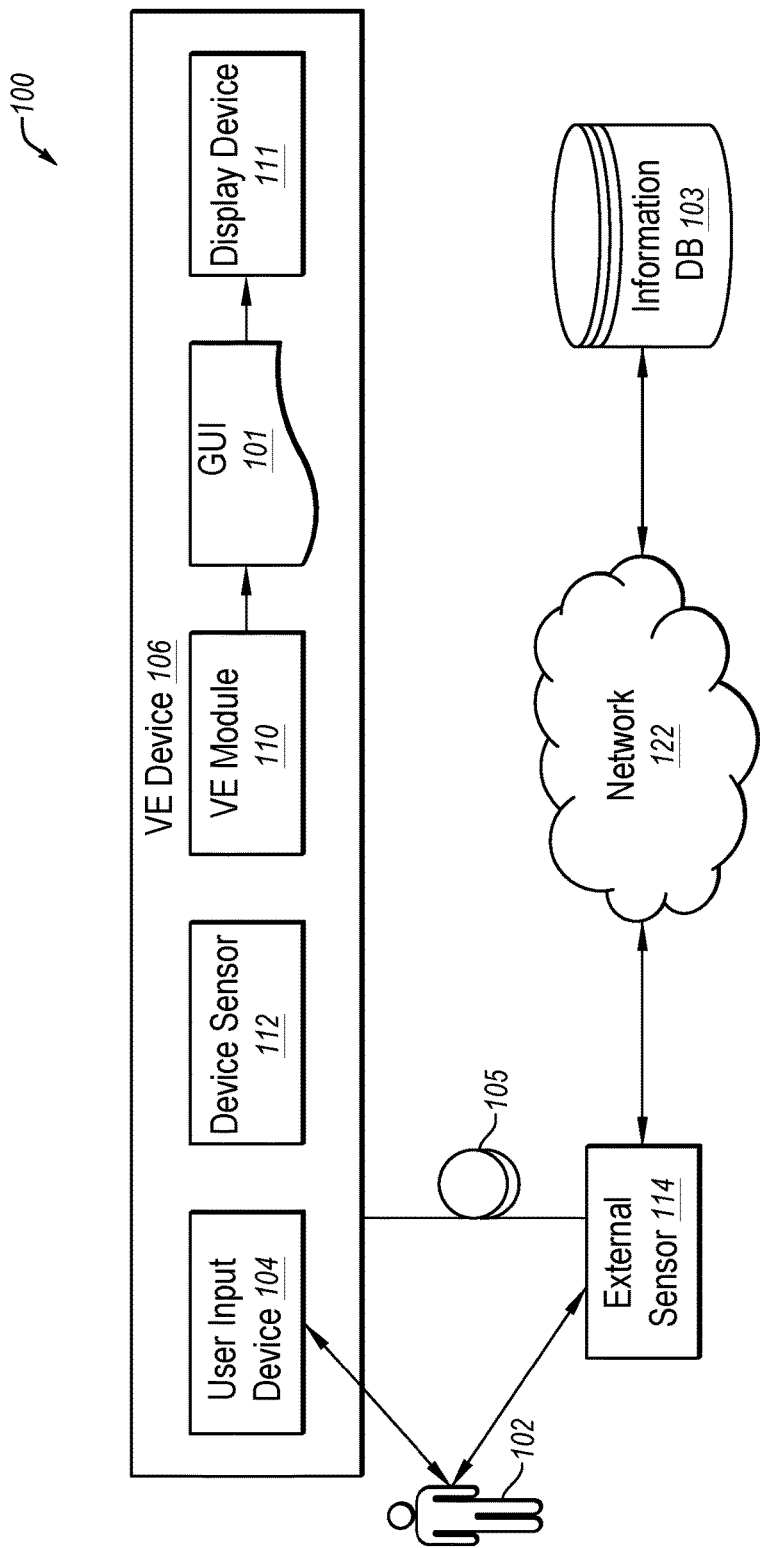
FIG. 1 is a block diagram of an example operating environment in which a virtual environment (VE) may be implemented.

FIG. 1 is a block diagram of an example operating environment 100 in which a virtual environment (VE) may be implemented. The VE implemented in the operating environment 100 may be based on a graphical user interface (GUI) 101. The GUI 101 may be generated by a VE device 106 for a user 102. The GUI 101 may include information that may affect behavior outcomes of the user 102. For example, the GUI 101 may flexibly present information that may trigger in the user 102 cognitive states that lead to improved behavior outcomes.

In some embodiments, the GUI 101 may be configured to trigger the cognitive state of scarcity. For example, the GUI 101 may present an overall time period such as the life of the user 102, which is inherently finite. Scarcity associated with the life of the user 102 and presented in the GUI 101 may motivate the user 102 to act.

The operating environment 100 of FIG. 1 may include the VE device 106, an information database (in FIG. 1, information DB) 103, an external sensor 114, a network 122, and the user 102. The VE device 106 may be configured to communicate with the external sensor 114 and/or the information database 103 via the network 122. For example, data measured by the external sensor 114 may be communicated from the external sensor 114 and the information database 103 to the VE device 106. The GUI 101 may be generated and/or updated based upon the data. In the following paragraphs, each of the VE device 106, the information database 103, the external sensor 114, the network 122, and the user 102 are described.

The network 122 may be wired or wireless, and may have configurations including a star configuration, token ring configuration, or other configurations. Furthermore, the network 122 may include a local area network (LAN), a wide area network (WAN) (e.g., the Internet), an internet of things, and/or other interconnected data paths across which multiple devices may communicate. The network 122 may also be coupled to or include portions of a telecommunications network that may enable communication of data in a variety of different communication protocols.

In some embodiments, the network 122 includes BLUETOOTH® communication networks and/or cellular communications networks for sending and receiving data including via short messaging service (SMS), multimedia messaging service (MMS), hypertext transfer protocol (HTTP), direct data connection, wireless application protocol (WAP), e-mail, etc. The network 122 may enable communication via a standard-based protocol (e.g., Wi-Fi, ZigBee, etc.).

The external sensor 114 may include any system or device that measures data relative to the user 102 and communicates data representative of measured data to the VE device 106. In the operating system 100 of FIG. 1, the external sensor 114 may be configured to provide at least a portion of input data to the VE device 106 based on which the GUI 101 is generated or updated. For example, to generate an initial version of the GUI 101, the external sensor 114 may measure some data and communicate data representative thereof to the VE device 106. Additionally or alternatively, following generation of the initial version of the GUI 101, the external sensor 114 may measure updated data, which may update the GUI 101. The external sensor 114 may be configured to communicate the data to the VE device 106 via the network 122 and/or a cable 105. Additionally, the VE device 106 may be configured to request or access data measured by the external sensor 114.

Some examples of the external sensor 114 may include a smart sensor. The smart sensors may include a processor and memory, which may store and process measured data prior to communication to the VE device 106. For example, the external sensor 114 may include a smart watch, a smart scale, a camera, a smart toothbrush, a thermometer, smart electrical outlets, a smart energy meter, exercise tracking sensors, caloric intake sensors, and the like. In some embodiments, the external sensor 114 may be included in a computing device such as a smart phone, a laptop computer, or some other computing device.

The type of external sensor 114 may be based on a type of the GUI 101 generated by the VE device 106. For instance, in some embodiments, the GUI 101 may be configured to depict a health and wellness strategy. In these and other embodiments, the external sensor 114 may include an exercise tracking sensor, a caloric intake sensor, and the like. In some embodiments, the GUI 101 is configured to depict an energy usage strategy. In these embodiments, the external sensor 114 may include a smart electrical outlet, a smart energy meter, and the like.

The information database 103 may include data and information that may be accessed by the VE device 106. For example, the VE device 106 may be configured to access data and information relative to the user 102 via the network 122. An example of the information database 103 may be a publically managed database that provides demographic information related to the user 102.

In the embodiment of FIG. 1, the information database 103 is separate from the VE device 106. In some embodiments, the information database 103 may be incorporated or partially incorporated in the VE device 106. Throughout this application data provided by the external sensor 114, a device sensor 112 (described below), and the information database 103 is referred to as machine contributed data.

The user 102 may include an individual or a group of individuals. For instance, the GUI 101 may be generated for a common goal of a group of individuals. The user 102 may interact with the VE device 106 and/or the external sensor 114. Interaction between the user 102 and the VE device 106 may include the GUI 101 being displayed visually to the user 102 on the display device 111. The interaction between the user 102 and the VE device 106 may also include the user 102 directly interacting with a user input device 104 to provide user contributed data to a user input device 104.

Interaction between the user 102 and the external device 114 may include the user 102 wearing the external sensor 114 or otherwise being implemented relative to the user 102 such that the external sensor 114 may measure behaviors or data related thereto of the user 102.

The VE device 106 may include any device that is capable of generating and updating the GUI 101 based on user contributed data and/or machine contributed data. The VE device 106 may generate the GUI 101 to create a connection between the user 102 and the VE device 106. The connection between the user 102 and the VE device 106 may influence behaviors of the user 102.

The GUI 101 may include a lightweight GUI. As used in this disclosure, "lightweight" may mean that the GUI 101 is relatively easy to build and customize for the user 102. For instance, the GUI 101 may include a low number (e.g., four or fewer) of shapes, two-dimensional shapes, little or no movement, simple icons, other simple features, or some combination thereof.

In addition, the GUI 101 may be configured to be effective to yield improved behavioral outcomes. For example, the GUI 101 may be configured to prime scarcity to the user 102. Scarcity as used in this disclosure to describe circumstances in which the user 102 feels that they have less of a resource than they feel that they need. Scarcity has been shown to be an effective motivating concept and may result in a "tunnel effect" or a focus dividend for the user 102. For example, the user 102 may be effective because the user focuses on addressing the scarcity.

Figure 4A:
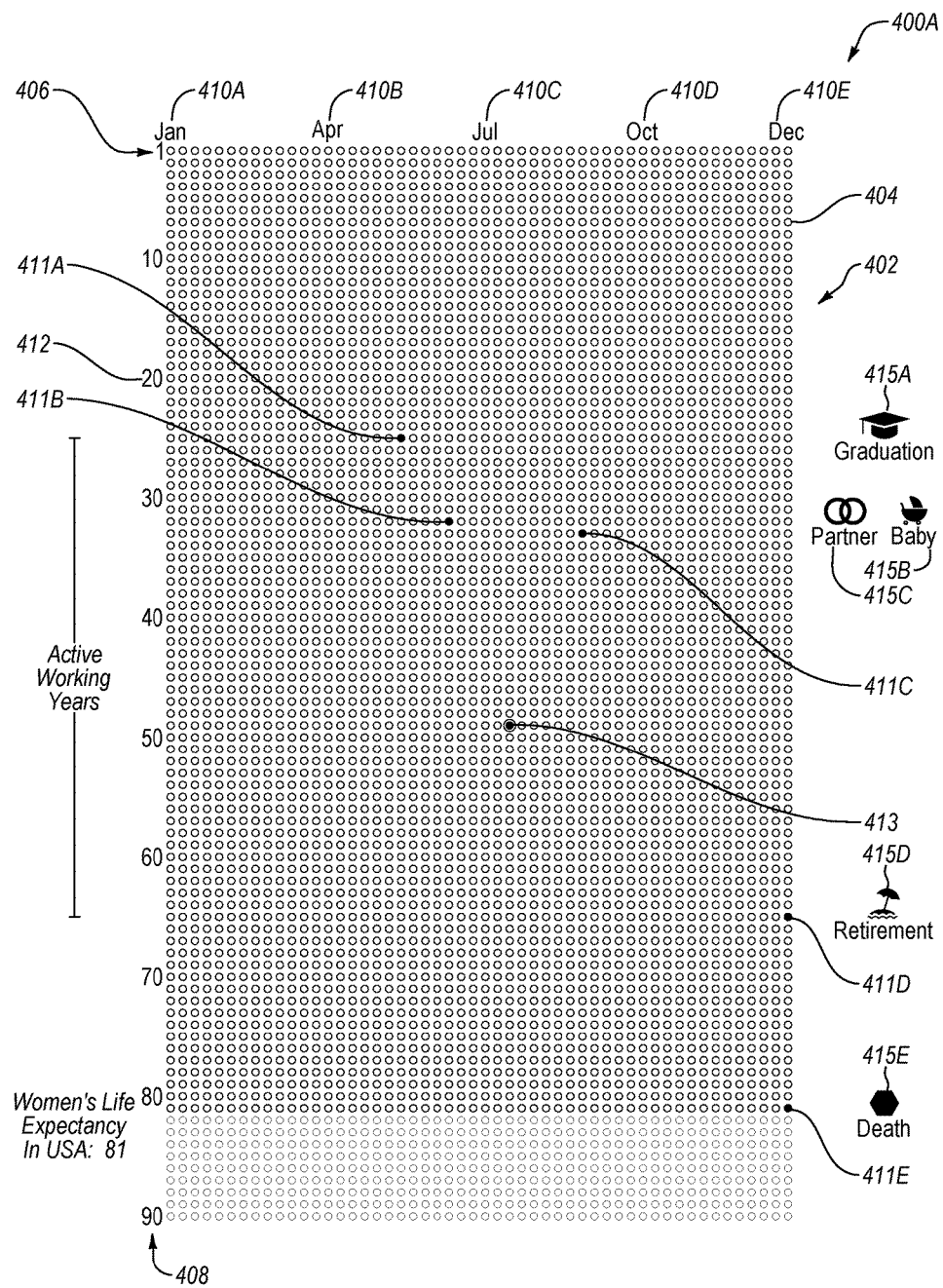
FIG. 4A illustrates an example GUI that may be generated and updated in the operating environment of FIG. 1.
Figure 4B:
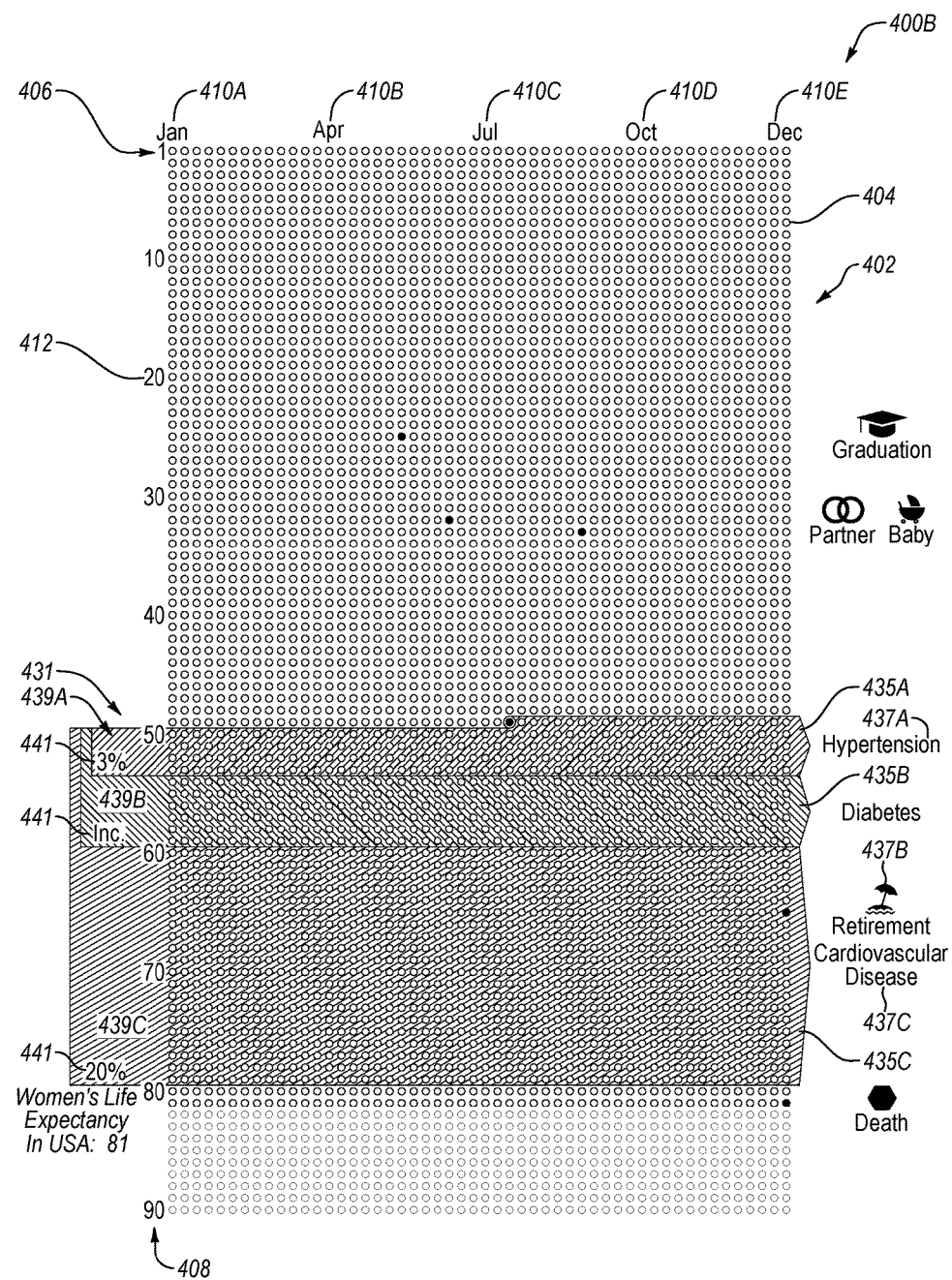
FIG. 4B illustrates another example GUI that may be generated and updated in the operating environment of FIG. 1.
Figure 4C:
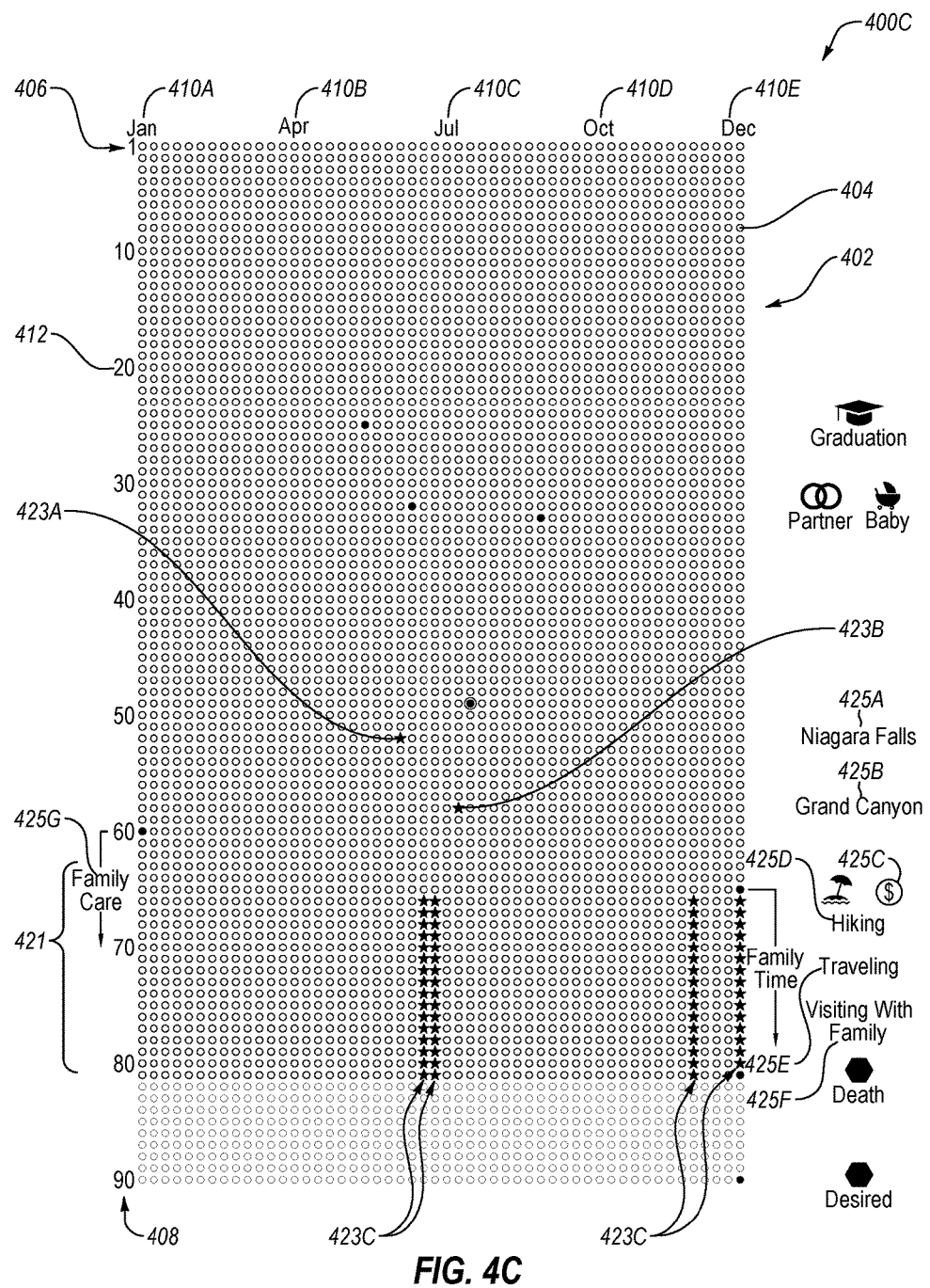
FIG. 4C illustrates another example GUI that may be generated and updated in the operating environment of FIG. 1.

In particular, the GUI 101 in some embodiments described in this disclosure primes scarcity of time and scarcity of opportunity. For instance, embodiments described in FIGS. 4A-4C are configured to prime scarcity in a life of the user 102. Some additional details of the embodiments of FIGS. 4A-4C are provided below. In these and other embodiments, the GUI 101 may be configured to prime scarcity of time and scarcity of opportunity prior to or following an event, an opportunity, a risk, or some combination thereof. For example, the GUI 101 may be configured to prime scarcity prior to or following a deadline (e.g., at an occupation), completion of a stage of life (e.g., retirement), a demand response event or energy assessment, a fitness goal or fitness activity, a social milestone, and a financial opportunity (e.g., debt consolidation).

The VE device 106 may include a user input device 104, a device sensor 112, a display device 111, and a VE module 110. Each of the user input device 104, the device sensor 112, the display device 111, and the VE module 110 are described below.

The user input device 104 may include one or more pieces of hardware configured to receive input from and/or provide output to the user 102. In some embodiments, the user input device 104 may include one or more of a speaker, a microphone, a display, a keyboard, a touch screen, or a holographic projection, among other hardware devices.

In the VE device 106 of FIG. 1, the user input device 104 may be configured to receive user contributed data as user input. The user input device 104 may be further configured to communicate the user contributed data to the VE module 110 such that the VE module 110 may generate and/or update the GUI 101 based thereon. In some embodiments, the user input device 104, may display a series or set of questions that the user 102 answers.

The device sensor 112 may be similar to the external sensor 114. However, the device sensor 112 may be included in the VE device 106 and thus communicate machine contributed data to the VE module 110 directly rather than via the network 122 and/or the cable 105.

The display device 111 may include any hardware device configured to receive the GUI 101 and display the GUI 101. The display device 111 may include a virtual-reality head unit, a two-dimensional display device, or a three-dimensional display device. For example, the display device 111 may include a cathode ray tube display (CRT), a light-emitting diode display (LED), an electroluminescent display (ELD), an electronic paper device, a plasma display panel (PDP), a liquid crystal display (LCD), an organic LED (OLED), a swept-volume display, a varifocal mirror display, an emissive volume display, or some combination thereof.

The VE module 110 may be configured to generate and update the GUI 101 based on the user contributed data and/or the machine contributed data (collectively, input data). The input data may be received from the user 102 via the user input device 104, the external sensor 114, the information database 103, the device sensor 112, or some combination thereof. The VE module 110 may generate the GUI 101 based on one or more portions of the input data.

For example, based on a first portion of the input data, the VE module 110 may render an initial icon arrangement of the GUI 101. The initial icon arrangement may include a set of icons that are each representative of a particular portion of an overall time period represented by the initial icon arrangement. The VE module 110 may also parse the input data for event data that includes a particular date and a particular type. The VE module 110 may generate a risk layer and/or an opportunity layer based on a second portion and/or a third portion of the input data. As used in this disclosure, the designation of portions of the input data as "first," "second," or "third" does not necessarily indicate a sequence. For example, in order for there to be a third portion, there does not necessarily need to be a second portion and the second portion does not need to be addressed before the third portion of the input data.

The VE module 110 may render event icons representative of the event data, the risk layer, the opportunity layer, the initial icon arrangement, or some combination thereof. The GUI 101 may include the rendered risk layer, the rendered opportunity layer, the rendered initial icon arrangement, or some combination thereof. The GUI 101 may be communicated to the display device 111. The display device 111 may display the GUI 101.

The VE module 110 may receive updated data. The updated data may include user contributed data and/or machine contributed data. The VE module 110 may dynamically re-render the risk layer, the opportunity layer, the event icons, or the initial icon arrangement based on the updated data.

The VE module 110 may be implemented using hardware including a processor, a microprocessor (e.g., to perform or control performance of one or more operations), a field-programmable gate array (FPGA), or an application-specific integrated circuit (ASIC). In some other instances, the VE module 110 may be implemented using a combination of hardware and software. Implementation in software may include rapid activation and deactivation of one or more transistors or transistor elements such as may be included in hardware of a computing system (e.g., the VE device 106). Additionally, software defined instructions may operate on information within transistor elements. Implementation of software instructions may at least temporarily reconfigure electronic pathways and transform computing hardware.

Modifications, additions, or omissions may be made to the operating environment 100 without departing from the scope of the present disclosure. The present disclosure may apply to operating environments that may include one or more VE devices 106, one or more external sensors 114, one or more users 102, one or more information databases 103, one or more networks 122, or any combination thereof. For example, the operating environment 100 may include multiple external sensors 114 that each contribute machine contributed data to the VE device 106.

Moreover, the separation of various components in the embodiments described herein is not meant to indicate that the separation occurs in all embodiments. It may be understood with the benefit of this disclosure that the described components may be integrated together in a single component or separated into multiple components. For example, the VE device 106 may include at least a portion of the information database 103.

Figure 2:
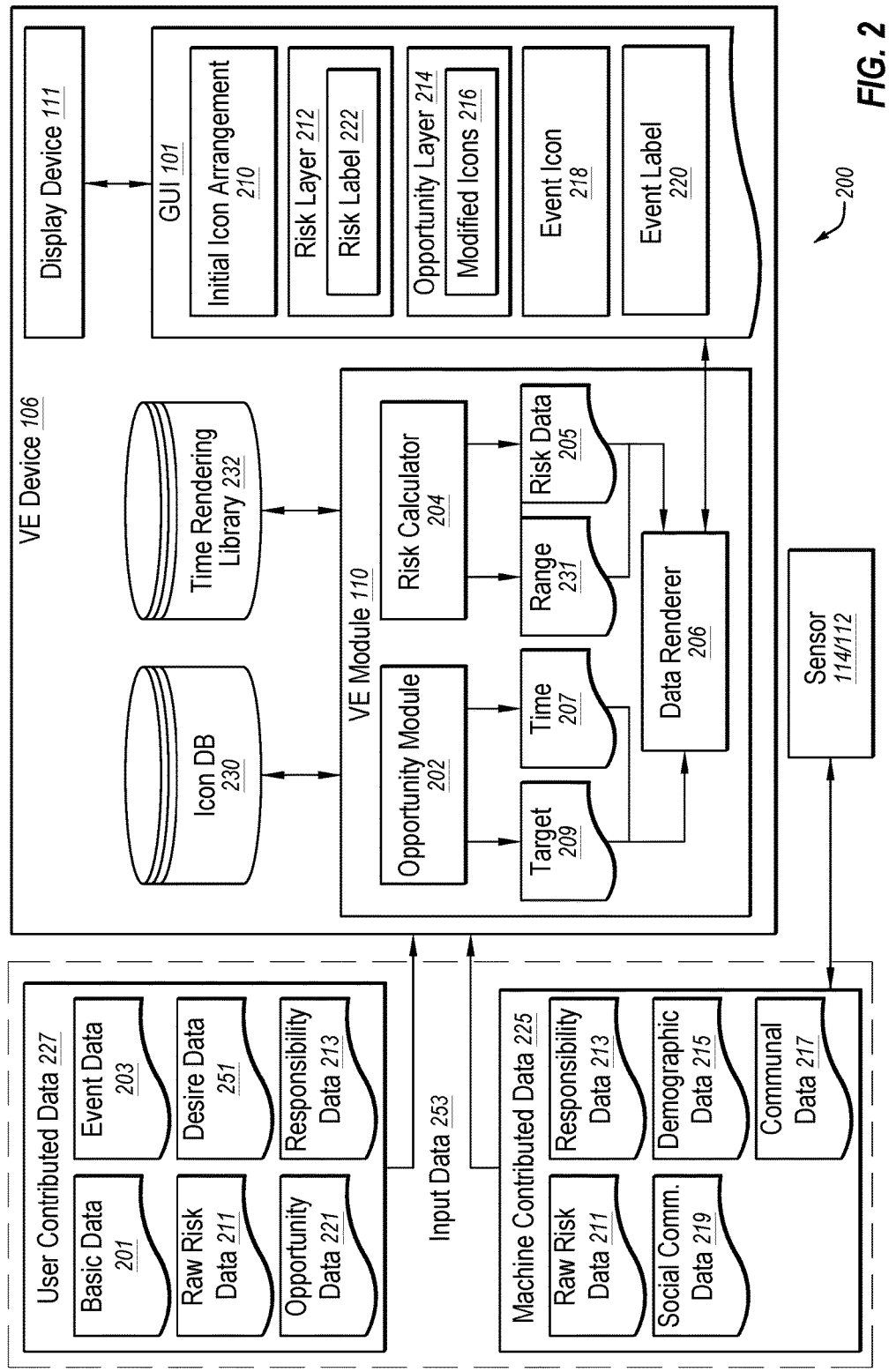
FIG. 2 represents an example graphic user interface (GUI) rendering process that may be implemented in the operating environment of FIG. 1.

FIG. 2 represents an example GUI rendering process 200 that may be implemented in the operating environment 100 of FIG. 1. The VE device 106, the external sensor 114, the device sensor 112 (collectively depicted in FIG. 2 as sensor 114/112), the display device 111, the GUI 101, and the VE module 110 of FIG. 1 are included in the GUI rendering process 200 of FIG. 2. In FIG. 2 example embodiments of the GUI 101 and the VE module 110 are depicted.

In the GUI rendering process 200, input data 253 may be communicated to or otherwise received by the VE device 106. Although not shown in FIG. 2, some portion of the input data 253 may be received via a network (e.g., the network 122 of FIG. 1). The input data 253 may include user contributed data 227 and machine contributed data 225.

As described above, the user contributed data 227 may be received at a user input device such as the user input device 104 of FIG. 1. The user contributed data 227 may include basic data 201, event data 203, raw risk data 211, desire data 251, opportunity data 221, and responsibility data 213.

The basic data 201 may include demographic data about a user. For example, the basic data 201 may include an age of the user, a gender of a user, an address of the user, and the like. The event data 203 may include data that pertains to events that have occurred in the past and may be considered important to a user. For example, the event data 203 may include data pertaining to graduation of the user, a relocation of the user, a marriage of the user, and the like. The raw risk data 211 may include data that pertains to a risk or a potential risk to the user. For example, raw risk data 211 may include medical information (e.g., blood pressure, cholesterol, and familial history); contractual information (e.g., minimum production); risk factors for developing a particular disease such as diabetes, hypertension, etc.; other personal information (e.g., weight and height), and the like. The desire data 251 may include events that a user desires for the future. For example, the desire data 251 may include places to travel, numbers associated with financial security, and the like. The opportunity data 221 may include data that pertains to an opportunity identified in the future for a user. For example, the opportunity data 221 may include a goal of spending time with a family of the user and the like. The responsibility data 213 may include data that represents a responsibility of the user. The responsibility data 213 may pertain to a past responsibility or to a future responsibility. For example, the responsibility data 213 may include data that pertains to paying for a college education for an offspring, providing care for a parent, and the like.

The machine contributed data 225 may include data that are representative of data or conditions measured by the sensors 114/112. Additionally or alternatively the machine contributed data 225 may be accessed or calculated by the VE device 106. For example, a portion of the machine contributed data 225 may be accessed from a public database such as the information database 103 of FIG. 1.

The machine contributed data 225 may include the raw risk data 211 and the responsibility data 213 described above. In addition, the machine contributed data 225 may include social communication data 219 (in FIG. 2, social comm. data 219), demographic data 215, and communal data 217. The social communication data 219 may be data that captures some event in the past of the user or in the future of the user. For example, the social communication data 219 may include dates of upcoming events (e.g., weddings, birthdays, etc.) or events that occurred (e.g., when a user met their spouse). The social communication data 219 may be derived from one or more social communications. For instance, the VE device 106 may access social communications from data feeds of social media accounts and/or access calendar events identified in a calendar application. The demographic data 215 may include data that are derived at a population level and that may be related to regional factors. An example of the demographic data 215 may include a life expectancy or a retirement date based on some portion of the basic data 201. The communal data 217 may include data that pertains to a common experience of a user and those similarly situated individuals according to custom or law. For example, the communal data 217 may include a number of days off received by the user.

The input data 253 may include other types of data. The types of data included in the input data 253 may depend on the strategy represented by the GUI 101. For example, in embodiments in which the GUI 101 includes an energy use strategy, the input data 253 (e.g., the machine contributed data 225) may include energy usage data from a smart meter associated with a user, a contractual provision (e.g., price) related to energy, an appliance list, and the like. In embodiments in which the GUI 101 depicts a financial strategy, the input data 253 may include a stock portfolio, a 401K match provision, and the like.

In the embodiment depicted in FIG. 2, the VE device 106 may include the VE module 110, the display device 111, and an icon database 230 (in FIG. 2, icon DB 230). The display device 111 may be substantially similar to the display device 111 described with reference to FIG. 1. The VE module 110 and the icon database 230 may be configured to generate the GUI 101 based on the input data 253 or some portions thereof.

The GUI 101 of FIG. 2 may include an initial icon arrangement 210, a risk layer 212, an opportunity layer 214, an event icon 218, and an event label 220. The VE module 110 may include an opportunity module 202, a risk calculator 204, and a data renderer 206. The data renderer 206 may be configured to render the GUI 101. For example, the data renderer 206 may render the initial icon arrangement 210, the risk layer 212, the opportunity layer 214, the event icon 218, the event label 220, or some combination thereof. The opportunity module 202 may be configured to process some portion of the input data 253 to generate data represented in the opportunity layer 214. Similarly, the risk calculator 204 may be configured to process some portion of the input data 253 to generate data represented in the risk layer 212.

For example, the data renderer 206 may receive a first portion of the input data 253. Based on the first portion of the input data 253, the initial icon arrangement 210 may be rendered. The initial icon arrangement 210 may be presentable in a virtual environment such as the operating environment 100 or some portion thereof. The initial icon arrangement 210 may include a set of icons that are each representative of a particular portion of an overall time period represented by the initial icon arrangement 210.

For example, an overall time period represented by the initial icon arrangement 210 may include a life of the user and each of the set of icons is representative of one week in the life of the user. In these and other embodiments, the icons in the set of icons may each include a circle or another simple shape organized into rows and columns to be displayed in the GUI 101.

The icons in the set of icons and their positions in the initial icon arrangement 210 may be stored in the icon database 230. In addition, a time related to one or more of the initial icon arrangement 210 may be stored in a time rendering library 232.

The data renderer 206 may be configured to parse the input data 253 for the event data 203. The event data 203 may include a particular date and a particular type. For example, the event data 203 may relate to a graduation of the user that may include a particular date (e.g., May 25, 2004) and a particular type (e.g., graduate degree graduation). The data renderer 206 may access the icon database 230 and the time rendering library 232 to determine which icon of the initial icon arrangement 210 corresponds to the event data 203. The data renderer 206 may replace the icon(s) that corresponds to the event data 203 with the event icon 218. Additionally, the data renderer 206 may further render the event label 220 that may indicate the particular type of the event data 203. A position of the event label 220 may be related to the event icon 218. For example, the event label 220 may be position directly to the side of the event icon 218 on the GUI 101.

In some embodiments, one or more of the event icon 218 may take a shape that is related to the particular type of the event data 203. For instance, a shape of the event icon 218 representative of the graduation may be a graduation cap. Similarly, a shape of the event icon 218 representative of a birth of an offspring may be a baby rattle or a stroller.

The opportunity module 202 may be configured to determine whether a second portion of the input data 253 is representable in the initial icon arrangement 210. For example, the opportunity module 202 may be configured to determine whether the opportunity data 221 in the input data 253 includes or may be represented as a date in the initial icon arrangement 210 and a target. In response to the second portion of the input data 253 being representable in the initial icon arrangement 210, the opportunity module 202 may quantify the second portion of the input data 253 with a target 209 and a timeframe (in FIG. 2 "time") 207.

For instance, the opportunity module 202 may access the icon database 230 and/or the time rendering library 232 to quantify the timeframe 207 and the target 209 for the second portion of the input data 253 in the initial icon arrangement 210. The time rendering library 232 may enable association of the timeframe 207 with a second portion of the input data 253. The icon database 230 may enable association of the target 209 with the second portion of the input data 253.

The opportunity module 202 may communicate the target 209 and the timeframe 207 associated with the second portion of the input data 253 to the data renderer 206. The data renderer 206 may modify and/or add one or more icons in the initial icon arrangement 210 that correspond to the timeframe 207 to represent the target 209. The data renderer 206 may further render the modified icons 216 or additional icons as the opportunity layer 214 on the initial icon arrangement 210.

The risk calculator 204 may determine whether a third portion of the input data 253 indicates a risk to the user (e.g., the user 102 of FIG. 1). For example, the third portion of the input data 253 may include the raw risk data 211, which may indicate a risk to the user. In response to the third portion of the input data 253 indicating the risk, the risk calculator 204 may further determine a range 231 of the icons of the initial icon arrangement 210 to which the risk pertains. For instance, the risk may include developing diabetes during the early fifties of the user. The range 231 of the icons of the initial icon arrangement 210 may accordingly include the icons corresponding to the early fifties of the user.

The risk calculator 204 may further generate risk data 205. The risk data 205 may include information related to the risk indicated by the third portion of the input data 253. For instance, the risk data 205 may include a type of the risk, a probability that a risk may occur, and the like. The risk calculator 204 may communicate the range 231 and the risk data 205 may be communicated to the data renderer 206. The data renderer 206 may render the risk layer 212 that includes the range 231 on the initial icon arrangement 210. The data renderer 206 may also render a risk label 222 on the initial icon arrangement 210. The risk label 222 may be indicative of the risk data 205 or some portion thereof.

Figure 3:
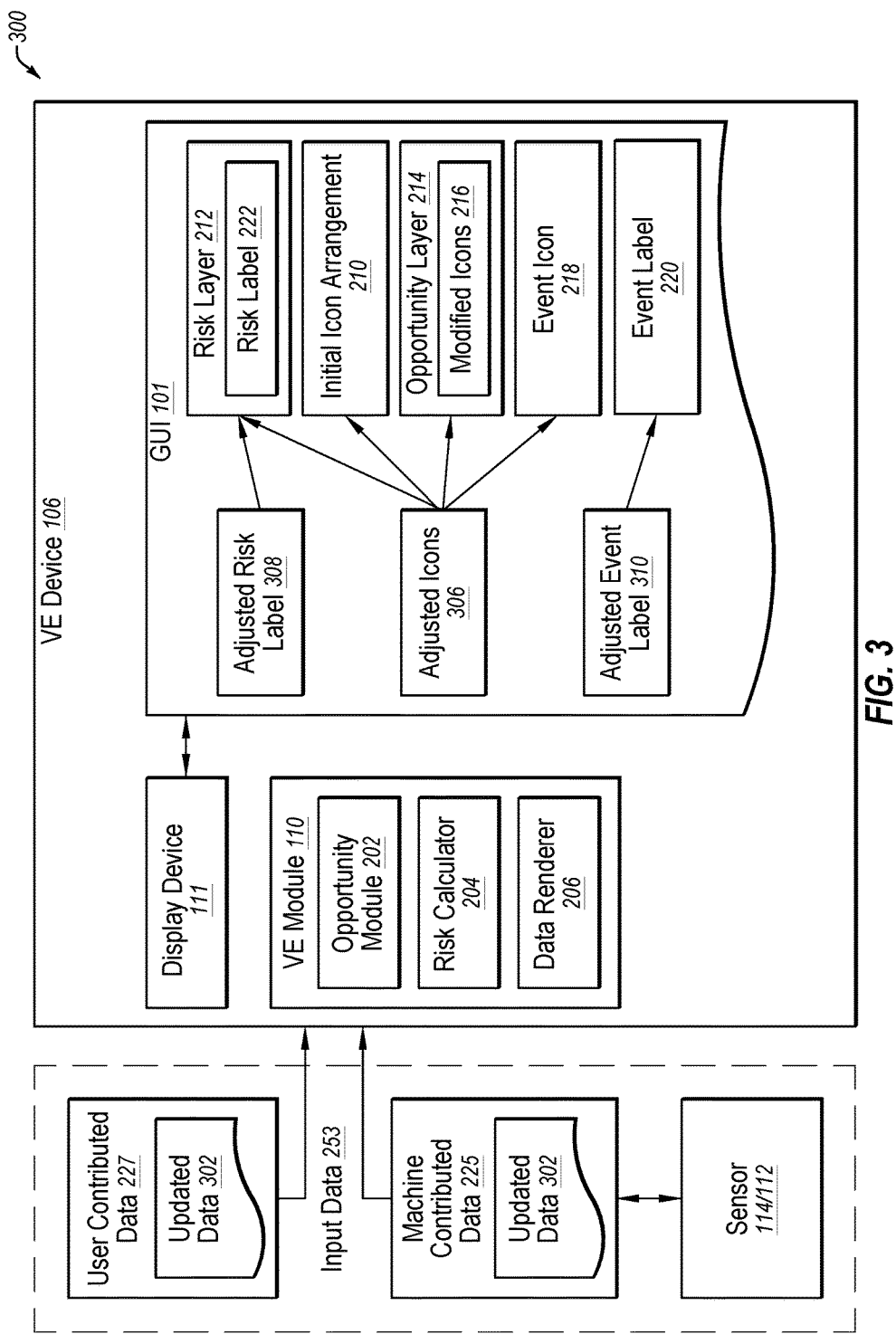
FIG. 3 represents an example GUI update process that may be implemented in the operating environment of FIG. 1.

FIG. 3 represents an example GUI update process 300 that may be implemented in the operating environment 100 of FIG. 1. The VE device 106, the sensor 114/112, the display device 111, and the VE module 110 of FIG. 2 are included in the GUI update process 300 of FIG. 3.

In the GUI update process 300, the input data 253 may include updated data 302. For example, the updated data 302 may be included in the user contributed data 227 and/or the machine contributed data 225. Although not shown in FIG. 3, some portion of the updated data 302 may be received via a network (e.g., the network 122 of FIG. 1).

The GUI update process 300 includes dynamically re-rendering the GUI 101 to include an adjusted risk label 308, one or more adjusted icons 306, an adjusted event label 310, or some combination thereof. For example, the adjusted risk label 308 may be dynamically re-rendered as the risk label 222 in the GUI 101. The adjusted icons 306 may be dynamically re-rendered as one or more of the risk layer 212, initial icon arrangement 210, the opportunity layer 214, the event icon 218 in the GUI 101. The adjusted event label 310 may be dynamically re-rendered as the event label 220 in the GUI 101. As used in this disclosure, dynamically re-rendered includes a real time or substantially real time update to the GUI 101.

The VE module 110 that includes the opportunity module 202, the risk calculator 204, and the data renderer 206 may be configured to determine whether the updated data 302 changes or alters information represented in the GUI 101.

For example, the data renderer 206 may determine whether the updated data 302 changes the first portion of the input data 253. In response to the updated data 302 changing the first portion of the input data 253, the data renderer 206 may adjust one or more icons in the set of icons to reflect the changes to the first portion of the input data 253. The data renderer 206 may dynamically re-render the adjusted icons 306 on the initial icon arrangement 210. Similarly, the data renderer 206 may parse the updated data 302 for updated event data (e.g., event data 203). The data renderer 206 may generate the adjusted event label 310 and dynamically re-render the GUI 101 to include the adjusted event label 310.

The risk calculator 204 may be configured to determine whether the updated data 302 alters the risk indicated by the third portion of the input data 253. In response to the updated data 302 altering the risk, the risk calculator 204 may adjust one or more icons in the risk range (e.g., range 231 of FIG. 2) and/or the risk label 222 to reflect the alteration to the risk. The adjusted icons 306 may be communicated from the risk calculator 204 to the data renderer 206. The data renderer 206 may dynamically re-render the adjusted icons 306 and/or the adjusted risk label 308 on the initial icon arrangement 210.

Similarly, the opportunity module 202 may determine whether the updated data 302 changes the second portion of the input data 253. In response to the updated data 302 changing the second portion of the input data 253, the opportunity module 202 may adjust the modified icons of the opportunity layer 214 to reflect the changes to the second portion of the input data 253. The adjusted modified icons may be communicated to the data renderer 206. The data renderer 206 may dynamically re-render the opportunity layer 214 with the adjusted icons 306.

One or more of the opportunity module 202, the risk calculator 204, and the data renderer 206 may be implemented using hardware including a processor, a microprocessor (e.g., to perform or control performance of one or more operations), an FPGA, or an ASIC. In some other instances, one or more of the opportunity module 202, the risk calculator 204, and the data renderer 206 may be implemented using a combination of hardware and software. Implementation in software may include rapid activation and deactivation of one or more transistors or transistor elements such as may be included in hardware of a computing system (e.g., the VE device 106). Additionally, software defined instructions may operate on information within transistor elements. Implementation of software instructions may at least temporarily reconfigure electronic pathways and transform computing hardware.

FIGS. 4A-4C illustrate example GUIs 400A, 400B, and 400C (generally, GUIs 400 or GUI 400). The GUIs 400 depicted in FIGS. 4A-4C may be examples of the GUI 101 discussed with reference to FIGS. 2 and 3. The GUIs 400 may be configured to affect a behavior outcome of a user (e.g., the user 102 of FIG. 1). For instance, the GUIs 400 may be configured to depict a health and wellness strategy for the user. In some other GUIs, an energy usage strategy, a financial health and wellness strategy, a social behavior strategy, a work and time management behavior strategy, or another strategy may be depicted in GUIs that include one or more features of the GUIs 400.

The GUIs 400 may prime a notion of scarcity for the user. For example, because the GUIs 400 may represent some overall time period along with risks, events, opportunities, or some combination thereof, the notion of scarcity may be conveyed by the GUIs 400. Accordingly, the GUIs 400 may be effective in changing the behavior of the user, avoiding a risk by the user, affecting a condition experience by the user, or assisting the user in meeting a goal.

With reference to FIG. 4A, a first GUI 400A may include an initial icon arrangement 402. The initial icon arrangement 402 may be rendered by a VE device such as the VE device 106 discussed elsewhere in this disclosure. The initial icon arrangement 402 may include a set of icons 404. One of the icons 404 are labeled in FIGS. 4A-4C.

The icons 404 may each be representative of a particular portion of an overall time period represented by the initial icon arrangement 402. For instance, in the embodiments of FIGS. 4A-4C the overall time period may be representative of the life of the user and each of the icons 404 may represent one week in the life of the user.

The icons 404 may be organized into rows 406 and columns 408. Each of the rows 406 may represent a year. In particular, in the depicted embodiments, month indicators 410A-410E may indicate a month in which the icons 404 are included. Similarly, year indicators 412 may indicate a year in which the icons 404 are included. Only one of the year indicators 412 are labeled in FIGS. 4A-4C. Accordingly, in the GUIs 400, the initial icon arrangement 402 may include the icons 404 ranging from a first year (e.g., the row 406 with year indicators 412 of '1') to a ninetieth year (e.g., the row 406 with a year indicator 412 of '90').

In other embodiments, the GUIs 400 may depict another overall time period such as a week, a month, a year, a decade, etc. In these and other embodiments, each of the icons 404 may represent some portion of the overall time period such as a day, an hour, etc.

In the depicted embodiments, the icons 404 may each include a circle. Additionally, the icons 404 may include a single color. In other embodiments, the icons 404 may each include another shape such as a square, triangle, and the like. Generally, the icons 404 may include simple icons that may be easily rendered.

The initial icon arrangement 402 may include a current day icon 413. The current day icon 413 may replace the icon 404 corresponding to a current day. For example, in FIG. 4A, a current day may include a third week in a forty-ninth year in the life of the user. Accordingly, the current day icon 413 may replace the icon 404 that is in the position in the initial icon arrangement 402 of the third week in the forty-ninth year.

The initial icon arrangement 402 may include one or more event icons 411A-411D. The event icons 411A-411D may be based on event data that are parsed from the input data discussed elsewhere in this disclosure. The event data may include a particular date. The particular date may include the date on which an event occurs, has occurred, or is likely to occur. For example, a first event may include a graduation event. The graduation may have occurred in the third week of May in a twenty-fifth year of the life of the user. A first event icon 411A may replace an icon 404 in the position in the initial icon arrangement 402 that corresponds to the third week of May in a twenty-fifth year.

Similarly, a second event may include a user death. The user death may likely occur in the final week of an eighty-first year of the life of the user. A fifth event icon 411E may replace an icon 404 in the position in the initial icon arrangement 402 that corresponds to the final week of an eighty-first year. The fifth event icon 411E represents a future event, which may be based on input data. For instance, the fifth event icon 411E may be based on a gender of the user, the geographic location of the user, and some outside information. For example, the fifth event icon 411E may be based on an average life expectancy of a woman in the United States of America.

The initial icon arrangement 402 may include one or more event labels 415A-415E (generally, event labels 415 or event label 415). The event labels 415 may include a particular type of one of the events. For example, a fifth event label 415E is death. The fifth event label 415E corresponds to the fifth event icon 411E described above.

The event icons 411 may be dynamically re-rendered based on one or more adjusted icons. The adjusted icons may be based on updated data that changes the input data on which the event icons 411 are based. For example, user contributed data may include a birth of a child, which may affect event data. Based on the user contributed data, adjusted icons that change the event icons 411 may be generated. The event icons 411 may be dynamically re-rendered including the adjusted icons.

FIG. 4B illustrates an example of a second GUI 400B. The second GUI 400B includes a risk layer 431 that is rendered on the initial icon arrangement 402 or some portion thereof. As discussed above, the risk layer 431 may be based on a third portion of the input data described elsewhere in this disclosure.

The risk layer 431 may be indicative of one or more risks to the user. For example, in FIG. 4B, the risk layer 431 includes three sub-risk layers 439A, 439B, and 439C (generally, sub-layer 439 or sub-layers 439). The sub-layers 439 may relate to one of the risks to the user. For instance, a first risk of hypertension may be represented in a first sub-layer 439A, a second risk of diabetes may be represented in a second sub-layer 439B, and a third risk of cardiovascular disease may be represented in a third sub-layer 439C. Other risks and other sub-layers 439 may be included in the risk layer 431 such as medical risks, financial risks, work/employment risks, and behavior risk.

The sub-layer 439 may include one or more ranges 435A-435C (generally, range 435 or ranges 435) of the icons 404. Each of the ranges 435 corresponds with a portion of the overall time period to which one of the risks applies and to the portion of the overall time period over which the sub-layer 439 is rendered. For instance, a first range 435A may correspond to the first risk of hypertension. The risk of hypertension may be greatest from about August of a forty-ninth year of the user's life until the fifty-fifth year of the user's life. Accordingly, the first sub-layer 439A is rendered over the icons 404 spanning over the first range 435A. Similarly, a second range 435B may correspond to the second risk of diabetes. The second risk of diabetes may be applicable from a fifty-fifth year in the user's life until a sixtieth year in the user's life. Accordingly, the second sub-layer 439B is rendered over the icons 404 spanning over the second range 435B.

One or more of the sub-layers 439 may include a different color, which may increase visibility relative to one another. The ranges 435 may overlap. For instance, the third sub-layer 439C may overlap the second sub-layer 439B and the first sub-layer 439A and the second sub-layer 439B may overlap the first sub-layer 439A. Additionally or alternatively, the sub-layers 439 may include other information 441 related to the risks represented in the sub-layers 439. The other information 441 may include a particular occurrence of the risk (e.g., a percentage), for instance.

In the embodiment of FIG. 4B, the risk layers 439 may include risk labels 437A-437C (risk label 437 or risk labels 437). The risk labels 437 may indicate a type of the risk illustrated by the sub-layer 439.

The risk layer 431 may be dynamically re-rendered based on one or more adjusted icons. The adjusted icons may be based on updated data that alters the risk indicated by the third portion of the input data. For example, sensors may indicate that the user's stress level is increasing, which may affect one or more of the ranges 435. Based on the increase, adjusted icons that change the ranges 435, the other information 441, the risk layer 431, etc may be generated. The sub-layers 439, the ranges 435, the other information 441, the risk layer 431, or some portions thereof may be dynamically re-rendered including the adjusted icons.

FIG. 4C illustrates an example of a third GUI 400C. The third GUI 400C includes an opportunity layer 421 that may be rendered on the initial icon arrangement 402 or some portion thereof. As discussed above, the opportunity layer 421 may be based on a second portion of the input data described elsewhere in this disclosure. The second portion of the input data included in the opportunity layer 421 may be representable parts of the second portion and accordingly may include a quantified timeframe and a quantified target.

The opportunity layer 421 may be indicative of one or more opportunities of the user. The opportunities are represented by one or more modified icons 423A-423C (generally, modified icon 423 or modified icons 423).

The modified icons 423 may replace the icons 404 and fill the position(s) in the initial icon arrangement 402 that correspond to the quantified timeframe and the quantified target that are associated with the opportunities. For example, a first modified icon 423A may represent a Niagara Falls trip opportunity. The Niagara Falls trip opportunity may be scheduled for a second week of June in a fifty-second year of the life of the user. Accordingly, the quantified timeframe and the qualified target associated with the Niagara Falls trip opportunity may be the second week of June in the fifty-second year of the life of the user. When the opportunity layer is rendered on the initial icon arrangement 402, the first modified icon 423A may replace a corresponding icon 404 that previously filled the position in the initial icon arrangement 402 for the second week of June in the fifty-second year.

Similarly, a second modified icon 423B may represent a Grand Canyon trip opportunity. The Grand Canyon trip opportunity may be scheduled for a first week of July in a fifty-eighth year of the life of the user. Accordingly, the quantified timeframe and the qualified target associated with the Grand Canyon trip opportunity may be the first week of July in the fifty-eighth year. Thus, when the opportunity layer is rendered on the initial icon arrangement 402, the second modified icon 423B may replace a corresponding icon 404 that previously filled the position in the initial icon arrangement 402 for the first week of July in the fifty-eighth year.

The quantified timeframe and the qualified target associated with some opportunities may include timeframe ranges and target ranges. For instance, a third modified icon set 423C may represent a family time opportunity. The family time opportunity may be based on geographic location, vacation time, holidays celebrated by the user, or some combination thereof. The family time opportunity may be scheduled for the last two weeks of June, the week of Thanksgiving, and the week of Christmas for the sixty-sixth year to the end of the life of the user (collectively, family weeks). Accordingly, the quantified timeframe and the qualified target associated with the family time opportunity may include the family weeks. Thus, when the opportunity layer is rendered on the initial icon arrangement 402, the third modified icon set 423C may replace corresponding icons 404 that previously filled the positions in the initial icon arrangement 402 of the family weeks.

In addition, the third GUI 400C may include opportunity labels 425A-425G (generally, opportunity labels 425 or 425 opportunity label). The opportunity labels 425 may indicate a type of opportunity that is represented by one or more of the modified icons 423. For example, a first opportunity label 425A "NIAGRA FALLS" may correspond to the first modified icon 423A that represents the Niagara Falls trip opportunity.

In the depicted embodiment, each of the modified icons 423 is a star. In other embodiments, one or more of the modified icons 423 may be one or more other shapes. Moreover, in some embodiments, one or more of the modified icons 423 may take shapes related to a type of the opportunity.

The opportunity layer 421 may be dynamically re-rendered based on one or more adjusted icons. The adjusted icons may be based on updated data that changes the second portion of the input data on which the modified icons 423 are based. For example, machine contributed data may indicate that the user's financial portfolio is increasing at a higher level than expected, which may affect one or more of the quantified timeframes or quantified targets represented by the modified icons 423. Based on the change, adjusted icons that change the modified icons 423 may be generated. The modified icons 423 or some portions thereof may be dynamically re-rendered including the adjusted icons.

Figure 5:
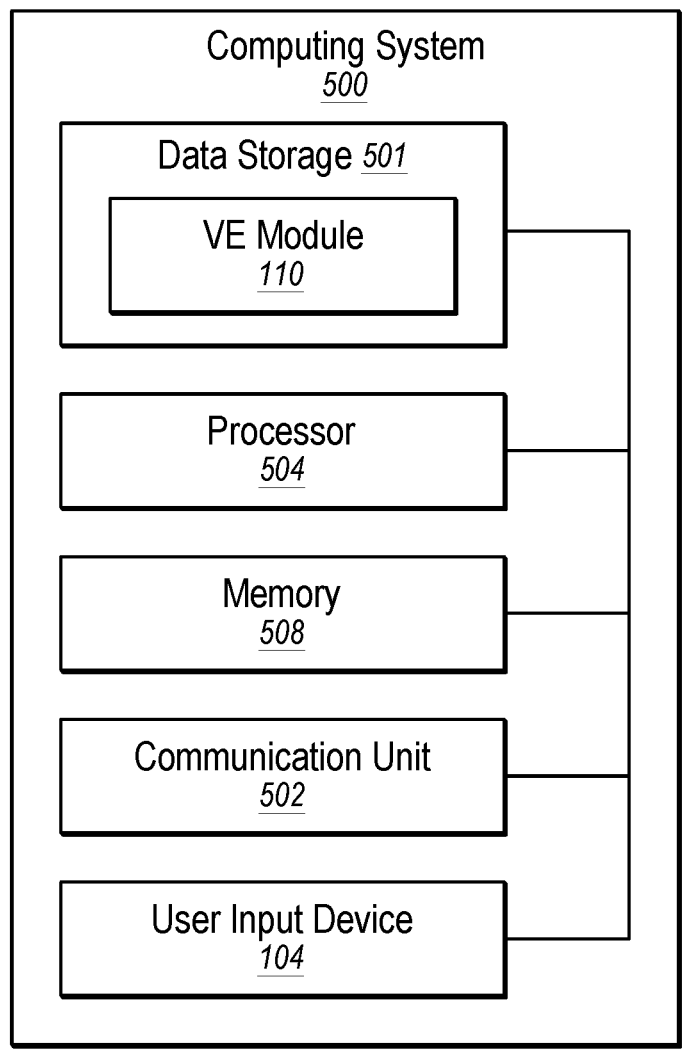
FIG. 5 illustrates an example computing system configured for GUI generation processes and/or GUI update processes.

FIG. 5 illustrates an example computing system 500 configured for generation and updating GUIs. The computing system 500 may be implemented in the operating system 100 of FIG. 1, for instance. Examples of the computing system 500 may include the VE device 106. The computing system 500 may include one or more processors 504, a memory 508, a communication unit 502, the user input device 104, and a data storage 501 that includes the VE module 110.

The processor 504 may include any suitable special-purpose or general-purpose computer, computing entity, or processing device including various computer hardware or software modules and may be configured to execute instructions stored on any applicable computer-readable storage media. For example, the processor 504 may include a microprocessor, a microcontroller, a digital signal processor (DSP), an ASIC, an FPGA, or any other digital or analog circuitry configured to interpret and/or to execute program instructions and/or to process data.

Although illustrated as a single processor in FIG. 5, the processor 504 may more generally include any number of processors configured to perform individually or collectively any number of operations described in the present disclosure. Additionally, one or more of the processors 504 may be present on one or more different electronic devices or computing systems. In some embodiments, the processor 504 may interpret and/or execute program instructions and/or process data stored in the memory 508, the data storage 501, or the memory 508 and the data storage 501. In some embodiments, the processor 504 may fetch program instructions from the data storage 501 and load the program instructions in the memory 508. After the program instructions are loaded into the memory 508, the processor 504 may execute the program instructions.

The memory 508 and the data storage 501 may include computer-readable storage media for carrying or having computer-executable instructions or data structures stored thereon. The term computer readable media may refer to a single medium or multiple media. Such computer-readable storage media may include any available media that may be accessed by a general-purpose or special-purpose computer, such as the processor 504. By way of example, and not limitation, such computer-readable storage media may include tangible or non-transitory computer-readable storage media including RAM, ROM, EEPROM, CD-ROM or other optical disk storage, magnetic disk storage or other magnetic storage devices, flash memory devices (e.g., solid state memory devices), or any other storage medium which may be used to carry or store desired program code in the form of computer-executable instructions or data structures and that may be accessed by a general-purpose or special-purpose computer. Combinations of the above may also be included within the scope of computer-readable storage media. Computer-executable instructions may include, for example, instructions and data configured to cause the processor 504 to perform a certain operation or group of operations.

Computer-executable instructions comprise, for example, instructions and data, which cause a general-purpose computer, special-purpose computer, or special-purpose processing resource to perform a certain function or group of functions. Although the subject matter has been described in language specific to structural features and/or methodological acts, it is to be understood that the subject matter defined in the appended claims is not necessarily limited to the specific features or acts described above. Rather, the specific features and acts described above are disclosed as example forms of implementing the claims.

The communication unit 502 may include one or more pieces of hardware configured to receive and send communications. In some embodiments, the communication unit 502 may include one or more of an antenna, a wired port, and modulation/demodulation hardware, among other communication hardware devices. In particular, the communication unit 502 may be configured to receive a communication from outside the computing system 500 and to present the communication to the processor 504 or to send a communication from the processor 504 to another device or network (e.g., 122 of FIG. 1).

The user input device 104 may include one or more pieces of hardware configured to receive input from and/or provide output to a user. In some embodiments, the user input device 104 may include one or more of a speaker, a microphone, a display, a keyboard, a touch screen, or a holographic projection, among other hardware devices.

The VE module 110 may include program instructions stored in the data storage 501. The processor 504 may be configured to load the VE module 110 into the memory 508 and execute the VE module 110. Alternatively, the processor 504 may execute the VE module 110 line-by-line from the data storage 501 without loading them into the memory 508. When executing the VE module 110, the processor 504 may be configured to perform a GUI generation process and/or GUI updating processes (e.g., method 600) as described elsewhere in this disclosure.

Modifications, additions, or omissions may be made to the computing system 500 without departing from the scope of the present disclosure. For example, in some embodiments, the computing system 500 may not include the user input device 104. In some embodiments, the different components of the computing system 500 may be physically separate and may be communicatively coupled via any suitable mechanism. For example, the data storage 501 may be part of a storage device that is separate from a server, which includes the processor 504, the memory 508, and the communication unit 502, that is communicatively coupled to the storage device.

FIGS. 6A-6D are a flowchart of a method 600 of rendering a GUI. The method 600 may be performed in an operating system such as the operating environment 100 of FIG. 1. The method 600 may be programmably performed in some embodiments by the VE device 106 described with reference to FIG. 1. In some embodiments, the VE device 106 or another computing system may include or may be communicatively coupled to a non-transitory computer-readable medium (e.g., the memory 508 of FIG. 5) having stored thereon programming code or instructions that are executable by one or more processors (such as the processor 504 of FIG. 5) to cause a computing system and/or the VE device 106 to perform or control performance of the method 600. Additionally or alternatively, the VE device 106 may include the processor 504 described above that is configured to execute computer instructions to cause the VE device 106 or another computing system to perform or control performance of the method 600. Although illustrated as discrete blocks, various blocks in FIG. 6 may be divided into additional blocks, combined into fewer blocks, or eliminated, depending on the desired implementation.

At block 602, input data may be received. The input data may be received at a VE device such as the VE device 106 described in this disclosure. The input data may pertain at least partially to a user such as the user 102. The input data may include user contributed data that are input to a user input device and/or machine contributed data measured at one or more sensors. For example, the input data may include user contributed data that are input by the user 102 into the user input device 104. Additionally or alternatively, the input data may include data measured or data representative of data measured by the device sensor 112 and/or the external sensor 114.

At block 604, a GUI may be rendered. The GUI may be based on a first portion of the input data. In some embodiments, the GUI may be rendered by a VE device such as the VE device 106 described in this disclosure. The GUI may include an initial icon arrangement that may be presentable in a virtual environment. In some embodiments, the initial icon arrangement includes a set of icons. One or more of the icons may be representative of a particular portion of an overall time period represented by the initial icon arrangement.

The initial icon arrangement may be configured to depict one or more or a combination of a health and wellness strategy, an energy usage strategy, a financial health and wellness strategy, a social behavior strategy, and a work and time management behavior strategy.

In some embodiments, the overall time period represented by the initial icon arrangement is the life of the user and each of the set of icons is representative of one week in the life of the user. Additionally or alternatively, one or more of the icons in the set of icons may include a circle. The circles may be organized into rows and columns.

At block 606, it may be determined whether a second portion of the input data is representable in the initial icon arrangement. In some embodiments, a VE device such as the VE device 106 or an opportunity module (e.g., 202) included therein may perform such determination. In response to the second portion of input data not being representable ("NO" at block 606), the method 600 may proceed to block 622. In response to the second portion of input data being representable ("YES" at block 606), the method 600 may proceed to block 608. At block 608, the second portion of the input data may be quantified with a target and a timeframe. For example, a VE device such as the VE device 106 may quantify the second portion of the input data 253 may be quantified with the target 209 and the timeframe 207.

At block 610, the target may be associated with the second portion of the input data. For example, a VE device such as the VE device 106 may associate the target 209 with the second portion. At block 612, the timeframe may be associated with the second portion of the input data. For example, a VE device such as the VE device 106 may associate the timeframe 207 with the second portion. At block 614, one or more icons may be modified. For example, one or more icons of the set of icons in the initial icon arrangement that correspond to the timeframe may be modified to represent the target. Additionally, in some embodiments, one or more icons may be added. For example, one or more icons of the set of icons in the initial icon arrangement may be added such that the target is represented.

Figure 6A:
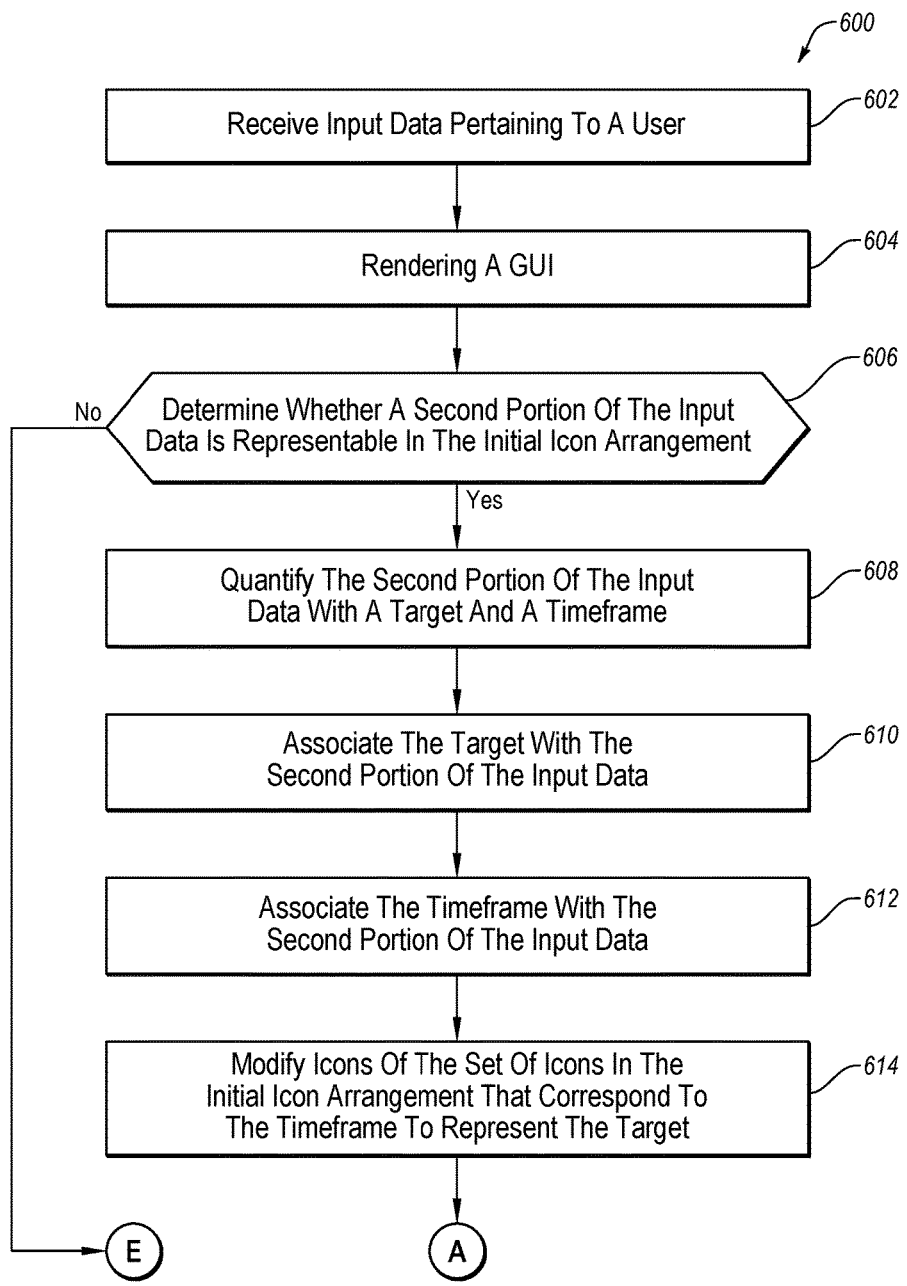
FIGS. 6A-6D are a flow diagram of an example method of GUI generation and/or GUI update, all arranged in accordance with at least one embodiment described herein.
Figure 6B:
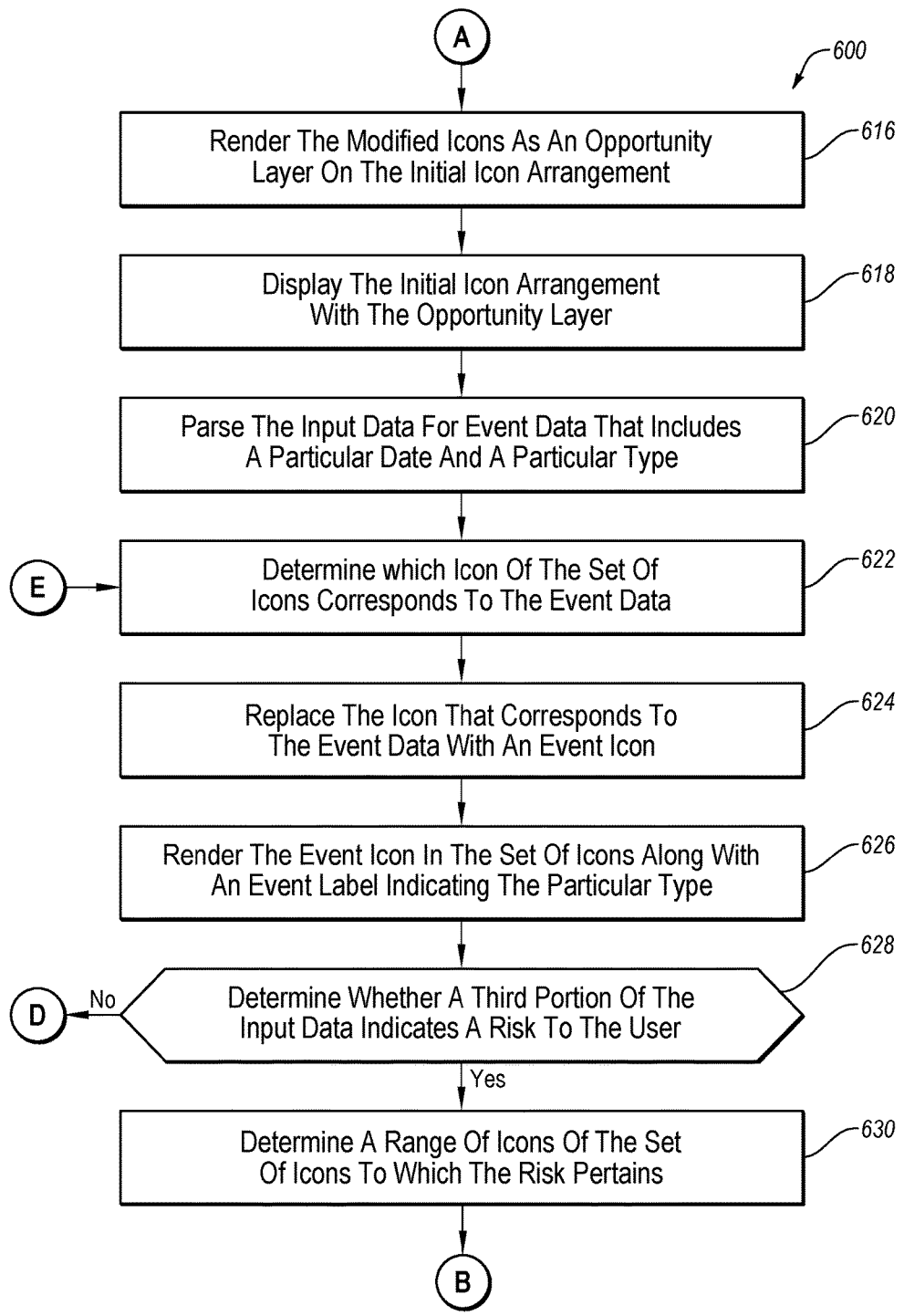

With reference to FIG. 6B, at block 616, the modified icons may be rendered as an opportunity layer on the initial icon arrangement. In some embodiments, a VE device such as the VE device 106 may render the modified icons 216 in the opportunity layer 214. At block 618, the initial icon arrangement may be displayed with the opportunity layer. For example, the initial icon arrangement may be displayed on a display device such as the display device 111 in the virtual environment.

At block 620, the input data may be parsed for event data. The event data may include a particular date and a particular type. At block 622 it may be determined which icon of the set of icons corresponds to the event data. At block 624, the icon that corresponds to the event data may be replaced with an event icon. At block 626, the event icon may be rendered in the set of icons along with an event label indicating the particular type.

At block 628, it may be determined whether a third portion of the input data indicates a risk to the user. In response to the third portion of the input data not indicating the risk ("NO" at block 628), the method 600 may proceed to block 638 of FIG. 6C. In response to the third portion of the input data indicating the risk ("YES" at block 628), the method 600 may proceed to block 630. At block 630, a range of icons may be determined of the set of icons to which the risk pertains.

Figure 6C:
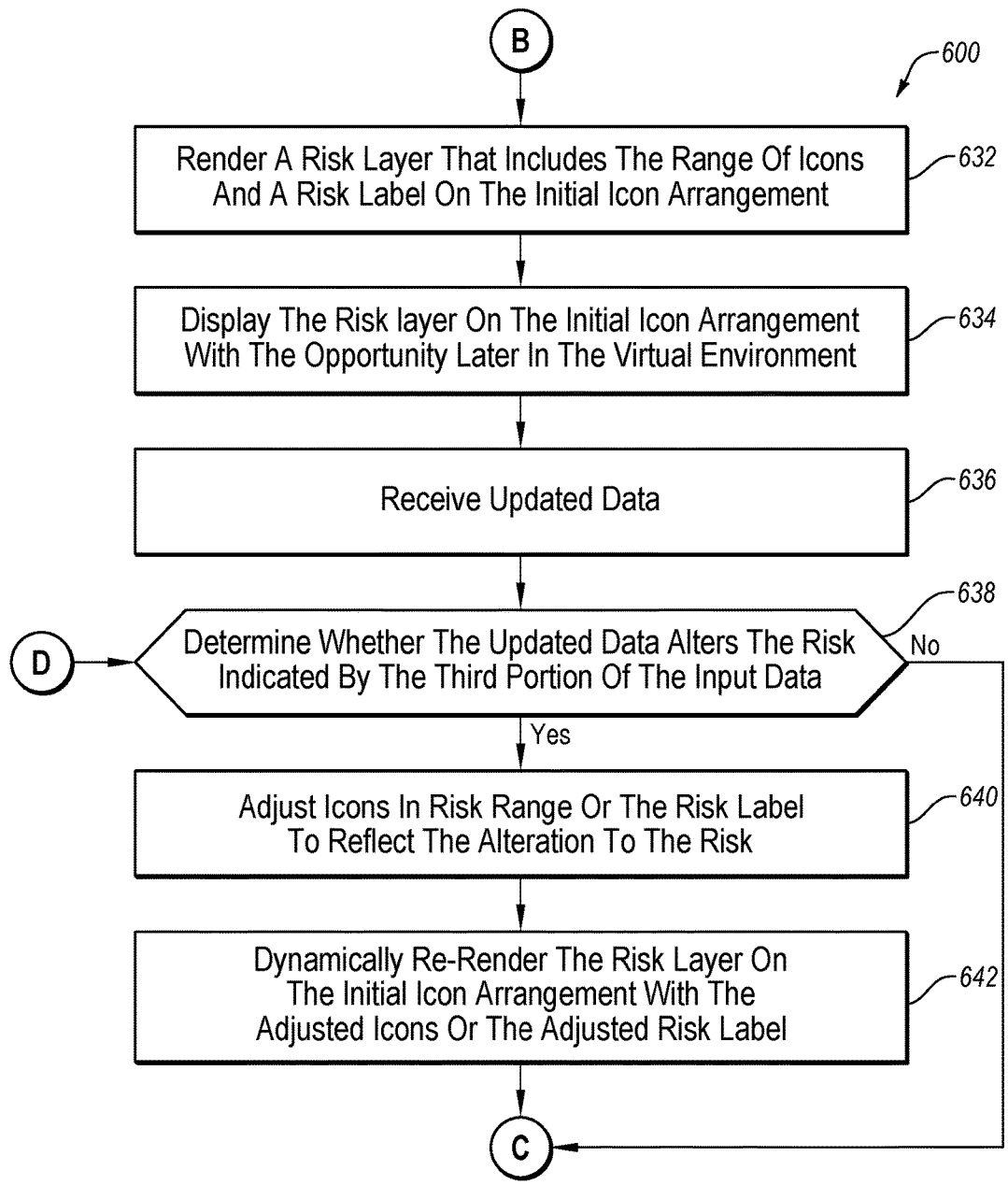

With reference to FIG. 6C, at block 632, a risk layer may be rendered. The risk layer may include the range of icons and a risk label on the initial icon arrangement. At block 634, the risk layer may be displayed on the initial icon arrangement with the opportunity layer in the virtual environment. At block 636, updated data may be received. The updated data may include user contributed data input to the user input device and machine contributed data measured at one or more sensors.

At block 638, it may be determined whether the updated data alters the risk indicated by the third portion of the input data. In response to the updated data not altering the risk ("NO" at block 638, the method 600 may proceed to block 644 of FIG. 6D. In response to the updated data altering the risk ("YES" at block 638), the method 600 may proceed to block 640. At block 640, one or more icons in risk range or the risk label may be adjusted to reflect the alteration to the risk. At block 642, the risk layer may be dynamically re-rendered on the initial icon arrangement with the adjusted icons and/or the adjusted risk label. In some embodiments, a data renderer such as the data renderer 206 of FIG. 3 may dynamically re-render the initial icon arrangement 210 with the adjusted icons 306.

Figure 6D:
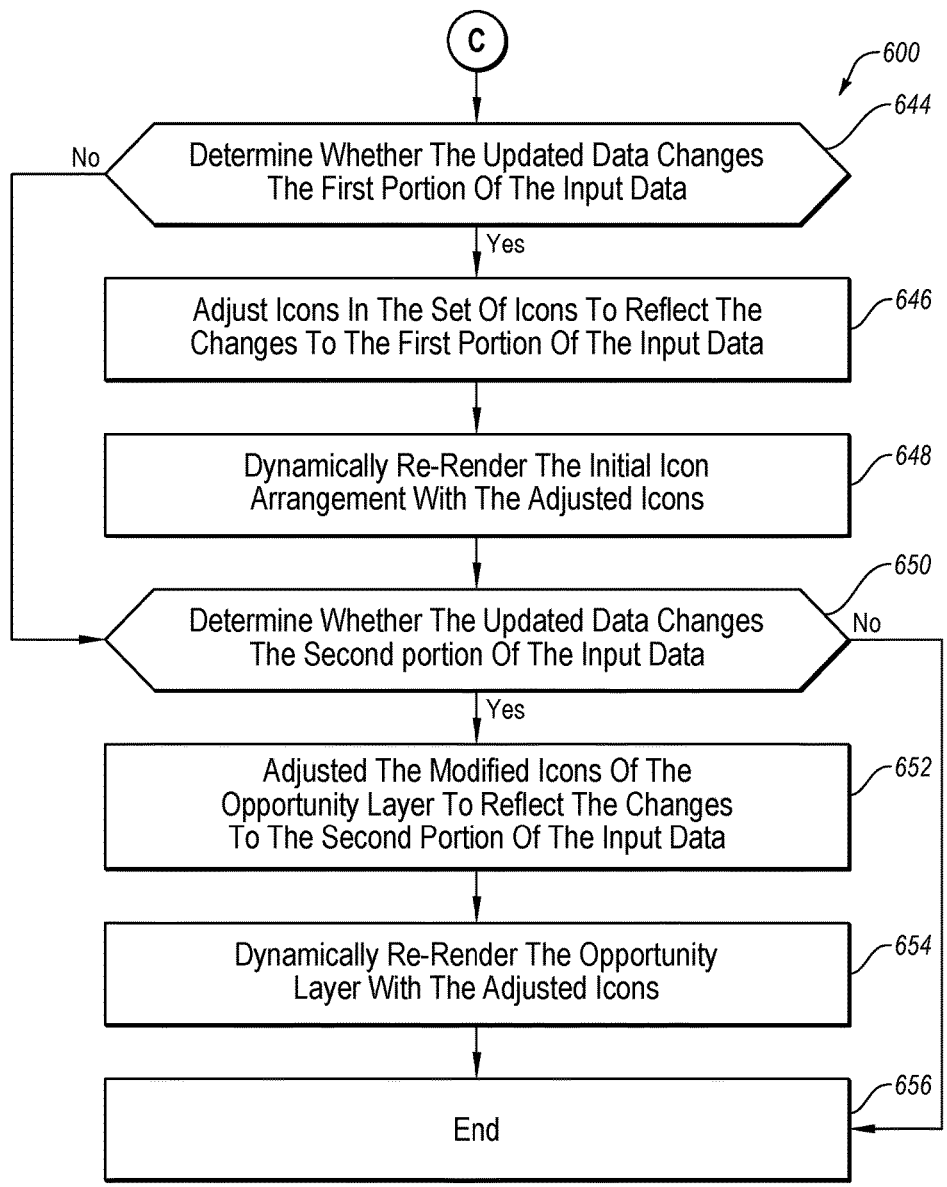

With reference to FIG. 6D, at block 644, it may be determined whether the updated data changes the first portion of the input data. In response to the updated data not changing the first portion of the input data ("NO" at block 644), the method 600 may proceed to block 650. In response to the updated data changing the first portion of the input data ("YES" at block 644), the method 600 may proceed to block 646. At block 646, one or more icons in the set of icons may be adjusted to reflect the changes to the first portion of the input data. At block 648, the initial icon arrangement may be dynamically re-rendered with the adjusted icons. In some embodiments, a data renderer such as the data renderer 206 of FIG. 3 may dynamically re-render the initial icon arrangement 210 with the adjusted icons 306.

At block 650, it may be determined whether the updated data changes the second portion of the input data. In response to the updated data not changing the second portion of the input data ("NO" at block 650), the method 600 may proceed to block 656 in which the method 600 may end. In response to the updated data changing the second portion of the input data ("YES" at block 650), the method 600 may proceed to block 652. At block 652, the modified icons of the opportunity layer may be adjusted to reflect the changes to the second portion of the input data. At block 654, the opportunity layer may be dynamically re-rendered with the adjusted icons. In some embodiments, a data renderer such as the data renderer 206 of FIG. 3 may dynamically re-render the opportunity layer 214 with the adjusted icons 306.

One skilled in the art will appreciate that, for this and other procedures and methods disclosed herein, the functions performed in the processes and methods may be implemented in differing order. Furthermore, the outlined steps and operations are only provided as examples, and some of the steps and operations may be optional, combined into fewer steps and operations, or expanded into additional steps and operations without detracting from the disclosed embodiments.

As used herein, the terms "module," "component," and/or "engine" may refer to software objects or routines that execute on the computing system. The different components, modules, engines, and services described herein may be implemented as objects or processes that execute on the computing system (e.g., as separate threads). While the system and methods described herein are preferably implemented in software, implementations in hardware or a combination of software and hardware are also possible and contemplated. In this description, a "computing entity" may be any computing system as previously defined herein, or any module or combination of modules running on a computing system.

All examples and conditional language recited herein are intended for pedagogical objects to aid the reader in understanding the invention and the concepts contributed by the inventor to furthering the art, and are to be construed as being without limitation to such specifically recited examples and conditions. Although embodiments of the present invention have been described in detail, it should be understood that the various changes, substitutions, and alterations could be made hereto without departing from the spirit and scope of the invention.

What is claimed is:

1. A method, comprising:
receiving, at a virtual environment (VE) device, input data pertaining to a user, the input data including user contributed data that are input to a user input device and machine contributed data that are measured at one or more sensors;
based on a first portion of the input data, rendering by the VE device, a graphical user interface (GUI) including an initial icon arrangement that is presentable in a virtual environment, wherein the initial icon arrangement includes a set of icons that are each representative of a particular portion of an overall time period represented by the initial icon arrangement;
determining, by the VE device, whether a second portion of the input data is representable in the initial icon arrangement;
in response to the second portion of input data being representable:
associating, by the VE device, a quantified target with the second portion of the input data;
further associating, by the VE device, a quantified timeframe with the second portion of the input data;
modifying, by the VE device, one or more icons in the initial icon arrangement that correspond to the timeframe to represent the target;
further rendering, by the VE device, the modified icons as an opportunity layer on the initial icon arrangement
on a display device,
wherein:
the set of icons each include a two-dimensional shape;
the set of icons is organized into rows and columns; and
the overall time period represented by the initial icon arrangement is a life of the user.

2. The method of claim 1, further comprising:
parsing the input data for event data that includes a particular date and a particular type;
determining which icon of the set of icons corresponds to the event data;
replacing the icon that corresponds to the event data with an event icon; and
further rendering the event icon in the set of icons along with an event label indicating the particular type.

3. The method of claim 1, further comprising:
determining whether a third portion of the input data indicates a risk to the user;
in response to the third portion of the input data indicating the risk:
further determining a range of icons of the set of icons to which the risk pertains;
further rendering a risk layer that includes the range of icons and a risk label on the initial icon arrangement; and
displaying the risk layer on the initial icon arrangement with the opportunity layer in the virtual environment.

4. The method of claim 3, further comprising:
receiving updated data, the updated data including user contributed data that are input to the user input device and machine contributed data measured at the one or more sensors;
determining whether the updated data alters the risk indicated by the third portion of the input data;
in response to the updated data altering the risk, adjusting one or more icons in risk range or the risk label to reflect the alteration to the risk; and
dynamically re-rendering the risk layer on the initial icon arrangement with the adjusted icons or the adjusted risk label.

5. The method of claim 1, further comprising:
receiving updated data, the updated data including user contributed data that are input to the user input device and machine contributed data that are measured at the one or more sensors;
determining whether the updated data changes the first portion of the input data;
in response to the updated data changing the first portion of the input data:
adjusting one or more icons in the set of icons to reflect the changes to the first portion of the input data; and
dynamically re-rendering the initial icon arrangement with the adjusted icons;
determining whether the updated data changes the second portion of the input data; in response to the updated data changing the second portion of the input data:
adjusting the modified icons of the opportunity layer to reflect the changes to the second portion of the input data; and
dynamically re-rendering the opportunity layer with the adjusted icons.

6. The method of claim 1, wherein
the set of icons each include a circle; and
each of the set of icons is representative of one week in the life of the user.

7. The method of claim 1, wherein the initial icon arrangement is configured to depict one or more or a combination of:
a health and wellness strategy;
an energy usage strategy;
a financial health and wellness strategy;
a social behavior strategy; and
a work and time management behavior strategy.

8. A non-transitory computer-readable medium having encoded therein programming code executable by one or more processors to perform or control performance of operations comprising:
receiving, at a virtual environment (VE) device, input data pertaining to a user, the input data including user contributed data that are input to a user input device and machine contributed data that are measured at one or more sensors;
based on a first portion of the input data, rendering by the VE device, a graphical user interface (GUI) including an initial icon arrangement that is presentable in a virtual environment, wherein the initial icon arrangement includes a set of icons that are each representative of a particular portion of an overall time period represented by the initial icon arrangement;

determining, by the VE device, whether a second portion of the input data is representable in the initial icon arrangement;

in response to the second portion of input data being representable:

associating, by the VE device, a quantified target with the second portion of the input data;

further associating, by the VE device, a quantified timeframe with the second portion of the input data;

modifying, by the VE device, one or more icons in the initial icon arrangement that correspond to the timeframe to represent the target;

further rendering, by the VE device, the modified icons as an opportunity layer on the initial icon arrangement on a display device, wherein:

the set of icons each include a two-dimensional shape;

the set of icons is organized into rows and columns; and the overall time period represented by the initial icon arrangement is a life of the user.

9. The non-transitory computer-readable medium of claim 8, further comprising:

parsing the input data for event data that includes a particular date and a particular type;

determining which icon of the set of icons corresponds to the event data;

replacing the icon that corresponds to the event data with an event icon; and further rendering the event icon in the set of icons along with an event label indicating the particular type.

10. The non-transitory computer-readable medium of claim 8, further comprising:

determining whether a third portion of the input data indicates a risk to the user;

in response to the third portion of the input data indicating the risk:

further determining a range of icons of the set of icons to which the risk pertains;

further rendering a risk layer that includes the range of icons and a risk label on the initial icon arrangement; and displaying the risk layer on the initial icon arrangement with the opportunity layer in the virtual environment.

11. The non-transitory computer-readable medium of claim 10, further comprising:

receiving updated data, the updated data including user contributed data that are input to the user input device and machine contributed data that are measured at the one or more sensors;

determining whether the updated data alters the risk indicated by the third portion of the input data;

in response to the updated data altering the risk, adjusting one or more icons in risk range or the risk label to reflect the alteration to the risk; and dynamically re-rendering the risk layer on the initial icon arrangement with the adjusted icons or the adjusted risk label.

12. The non-transitory computer-readable medium of claim 8, further comprising:

receiving updated data, the updated data including user contributed data that are input to the user input device and machine contributed data that are measured at the one or more sensors;

determining whether the updated data changes the first portion of the input data;

in response to the updated data changing the first portion of the input data:

adjusting one or more icons in the set of icons to reflect the changes to the first portion of the input data; and dynamically re-rendering the initial icon arrangement with the adjusted icons;

determining whether the updated data changes the second portion of the input data; in response to the updated data changing the second portion of the input data:

adjusting the modified icons of the opportunity layer to reflect the changes to the second portion of the input data; and dynamically re-rendering the opportunity layer with the adjusted icons.

13. The non-transitory computer-readable medium of claim 8, wherein:

the set of icons each include a circle; and each of the set of icons is representative of one week in the life of the user.

14. The non-transitory computer-readable medium of claim 8, wherein the initial icon arrangement is configured to depict one or more or a combination of:

a health and wellness strategy;

an energy usage strategy;

a financial health and wellness strategy;

a social behavior strategy; and a work and time management behavior strategy.

15. A graphical user interface (GUI) configured to affect a behavior outcome of a user, the GUI comprising:

an initial icon arrangement rendered by a virtual environment (VE) device on a display device of the VE device, the initial icon arrangement including a set of icons that are each representative of a particular portion of an overall time period represented by the initial icon arrangement and the initial icon arrangement being based on a first portion of input data pertaining to the user; and an opportunity layer that includes modified icons rendered on the initial icon arrangement, the modified icons being representative of a second portion of the input data that are representable in the initial icon arrangement and an associated quantified timeframe and associated quantified target of the second portion of the input data, wherein:

the input data includes user contributed data input to a user input device and machine contributed data measured at one or more sensors;

the set of icons each include a two-dimensional shape;

the set of icons is organized into rows and columns; and the overall time period represented by the initial icon arrangement is a life of the user.

16. The GUI of claim 15, further comprising:

an event icon that replaces one or more of the icons in the set of icons; and an event label, wherein:

the event icon is based on event data that are parsed from the input data; and the event data includes a particular date that corresponds to the one or more of the icons replaced by the event icon and a particular type that is represented by the event label.

17. The GUI of claim 16, further comprising:
a risk layer that is based on a third portion of the input data that are indicative of a risk to the user, wherein:
  the risk layer includes a range of icons of the set of icons to which the risk pertains and a risk label representing a type of the risk, and
  the risk layer is rendered on the initial icon arrangement over the range of icons.

18. The GUI of claim 17, further comprising:
adjusted icons that are dynamically re-rendered as portions of one or more or a combination of the risk layer, the opportunity layer, the event icon, or the initial icon arrangement, wherein:
the adjusted icons are based on updated data that alters the risk indicated by the third portion of the input data, changes the first portion of the input data, or changes the second portion of the input data; and
the updated data includes user contributed data that are input to the user input device and machine contributed data measured at the one or more sensors.

19. The GUI of claim 15, wherein
the set of icons each include a circle; and
each of the set of icons is representative of one week in the life of the user.

20. The GUI of claim 15, wherein the initial icon arrangement is configured to depict one or more or a combination of:
  a health and wellness strategy;
  an energy usage strategy;
  a financial health and wellness strategy;
  a social behavior strategy; and
  a work and time management behavior strategy.

* * * * *